United States Patent
Sahoyama et al.

(10) Patent No.: US 9,657,286 B2
(45) Date of Patent: May 23, 2017

(54) PRE-PROCESSING/ELECTROPHORESIS INTEGRATED CARTRIDGE, PRE-PROCESSING INTEGRATED CAPILLARY ELECTROPHORESIS DEVICE, AND PRE-PROCESSING INTEGRATED CAPILLARY ELECTROPHORESIS METHOD

(71) Applicant: Hitachi High-Technologies Corporation, Tokyo (JP)

(72) Inventors: Yukari Sahoyama, Tokyo (JP); Motohiro Yamazaki, Tokyo (JP); Yoshitaka Kodama, Tokyo (JP); Takamichi Muramatsu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 182 days.

(21) Appl. No.: 14/416,146

(22) PCT Filed: Jun. 11, 2013

(86) PCT No.: PCT/JP2013/066041
§ 371 (c)(1),
(2) Date: Jan. 21, 2015

(87) PCT Pub. No.: WO2014/017193
PCT Pub. Date: Jan. 30, 2014

(65) Prior Publication Data
US 2015/0210999 A1    Jul. 30, 2015

(30) Foreign Application Priority Data
Jul. 23, 2012   (JP) .................................. 2012-162685

(51) Int. Cl.
*G01N 27/447* (2006.01)
*C12N 15/10* (2006.01)
(Continued)

(52) U.S. Cl.
CPC .......... *C12N 15/101* (2013.01); *B01L 3/5027* (2013.01); *B01L 7/52* (2013.01);
(Continued)

(58) Field of Classification Search
CPC ... B01L 3/5027–3/502792; B81B 1/00–1/008; G01N 27/447–27/44795
(Continued)

(56) References Cited

U.S. PATENT DOCUMENTS

| 5,366,608 A | 11/1994 | Kambara |
| 2004/0173460 A1 | 9/2004 | Yamamoto et al. |

(Continued)

FOREIGN PATENT DOCUMENTS

| EP | 1867733 | 12/2007 |
| JP | 2003-177114 A | 6/2003 |

(Continued)

OTHER PUBLICATIONS

Japanese Office Action received in corresponding Japanese Application No. 2012-162685 dated Mar. 1, 2016.

*Primary Examiner* — Bach Dinh
(74) *Attorney, Agent, or Firm* — Mattingly & Malur, PC (57) ABSTRACT

To allow fully automated implementation of all steps of from pre-processing up to electrophoresis. Provided is a pre-processing/electrophoresis integrated cartridge including one or more block structures corresponding to the individual steps of pre-processing. Each block structure includes (1) a first block having a reaction tank, a reagent tank, a plurality of flow channels that connect the tanks, a plurality of control valves arranged in the flow channels, and a flow channel that connects a reaction tank in a block structure located at a preceding stage and a reaction tank in a block structure located at a next stage, and (2) a second block having a phoretic solution tank, a cathode buffer solution tank, a wash (Continued)

solution tank, a flow channel that connects a carrier tank in the block structure located at the preceding stage and the phoretic solution tank, and a control valve for the flow channel.

10 Claims, 9 Drawing Sheets (51) Int. Cl.
B01L 3/00 (2006.01)
C12Q 1/68 (2006.01)
B01L 7/00 (2006.01)

(52) U.S. Cl.
CPC ........... *C12Q 1/6806* (2013.01); *C12Q 1/686* (2013.01); *G01N 27/44791* (2013.01); *B01L 2200/028* (2013.01); *B01L 2200/10* (2013.01); *B01L 2300/0816* (2013.01); *B01L 2400/0421* (2013.01); *B01L 2400/0487* (2013.01)

(58) Field of Classification Search
USPC ................ 204/450–470, 547–549, 600–621, 204/644–645
See application file for complete search history.

(56) References Cited

U.S. PATENT DOCUMENTS

2004/0223874 A1 11/2004 Numajiri
2010/0213063 A1* 8/2010 Zenhausern ......... G01N 21/645
204/452

FOREIGN PATENT DOCUMENTS

JP 2004-301767 10/2004
JP 2007-330179 12/2007
WO 02/090968 11/2002

* cited by examiner

PRE-PROCESSING/ELECTROPHORESIS INTEGRATED CARTRIDGE, PRE-PROCESSING INTEGRATED CAPILLARY ELECTROPHORESIS DEVICE, AND PRE-PROCESSING INTEGRATED CAPILLARY ELECTROPHORESIS METHOD

TECHNICAL FIELD

The present invention relates to a pre-processing/electrophoresis integrated cartridge (i.e., an integrated sample preparation and electrophoresis device) that can be used for all steps of from pre-processing, such as extracting nucleic acids from a biological sample and amplifying and labeling the nucleic acids, up to electrophoresis, and a pre-processing integrated capillary electrophoresis apparatus (i.e., an integrated sample preparation and electrophoresis apparatus) and a pre-processing integrated capillary electrophoresis method (i.e., an integrated sample preparation and electrophoresis method) that can fully automatically execute all steps.

BACKGROUND ART

Methods for diagnosing genes or analyzing biological samples on the genetic level, such as DNA analysis, typically include the following sequential steps: (1) a pre-processing reaction stage including a step of extracting nucleic acids from a biological sample, a step of amplifying the extracted nucleic acids, and a step of labeling the nucleic acids, and (2) an electrophoresis stage of sequentially reading the base sequences of the nucleic acids after the pre-processing. In each stage, a plurality of reagents are mixed, heated, and dispensed. Thus, lots of work are needed to conduct analysis.

In order to increase the workability, a method for automatically executing an operation that is needed in each pre-processing step on a cartage, which incorporates storage tanks, flow channels, and the like for a developing solution, is known (for example, see Patent Literature 1).

In order to perform electrophoresis of nucleic acids, a capillary electrophoresis device is typically used. Patent Literature 2 describes an example of the conventional capillary electrophoresis device.

CITATION LIST

Patent Literature

Patent Literature 1: JP 2007-330179 A
Patent Literature 2: U.S. Pat. No. 5,366,608 A

SUMMARY OF INVENTION

Technical Problem

However, although Patent Literature 1 describes a technique of automating each step of gene analysis, such technique is not based on the assumption of entirely automating a series of operations for obtaining base sequences from a biological sample or from nucleic acids through electrophoresis. Therefore, the conventional techniques always involve an operation of transporting a cartridge or a sample, which is used in each step, to a corresponding device, and thus require complex operations.

Accordingly, the present invention provides a technology that can fully automate a series of operations of from the stage of extracting nucleic acids from a sample solution or from the subsequent pre-processing stage of amplifying and labeling the nucleic acids up to the electrophoresis stage of reading the base sequences of the nucleic acids.

Solution to Problem

The present invention provides an integrated cartridge that can be used for a series of reactions of from pre-processing, which includes one or more steps, up to electrophoresis, and a pre-processing integrated capillary electrophoresis device and method for implementing, with the use of such cartridge, a series of reactions of from pre-processing up to electrophoresis using a single device.

Advantageous Effects of Invention

According to the present invention, a series of reactions of from pre-processing up to electrophoresis can be executed with a single device and a single cartridge. Thus, improved operability is expected. Other problems, configurations, and advantages will become apparent from the following description of embodiments.

DESCRIPTION OF EMBODIMENTS

Hereinafter, embodiments of the present invention will be described with reference to the drawings. It should be noted that embodiments of the present invention are not limited to those described below, and a variety of variations are possible within the spirit and scope of the present invention.

Embodiment 1

Figure 1:
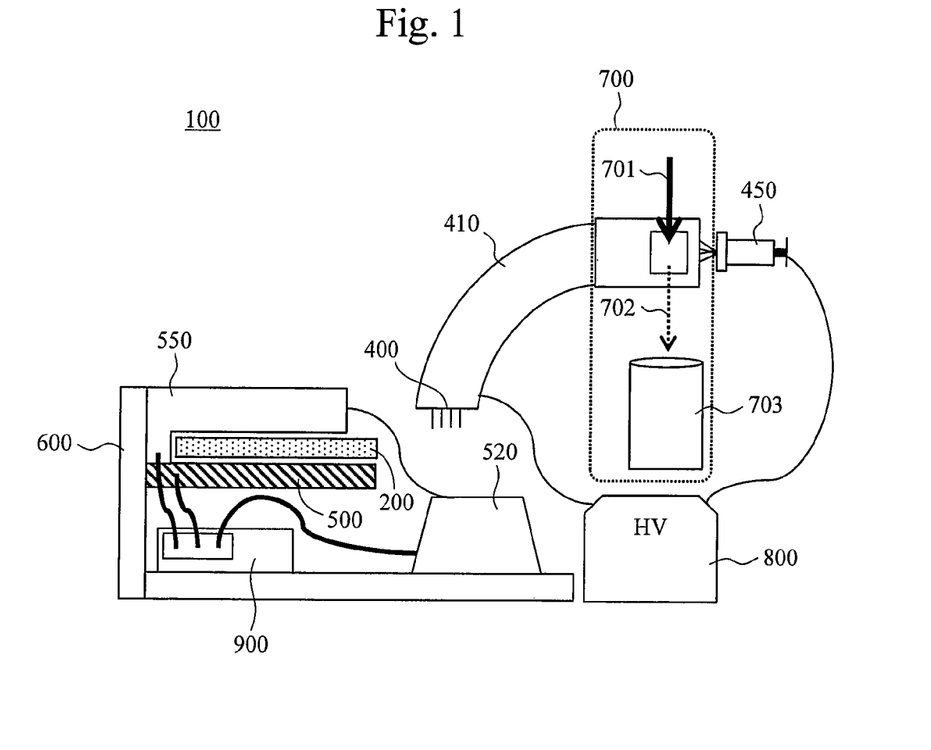
FIG. 1 shows an exemplary configuration of a pre-processing integrated capillary electrophoresis device in accordance with Embodiment 1.

Configuration of Pre-Processing Integrated Capillary Electrophoresis Device FIG. 1 shows the configuration of a pre-processing integrated capillary electrophoresis device 100 in accordance with Embodiment 1. The pre-processing integrated capillary electrophoresis device 100 is a device that fully automatically executes a series of reactions/operations of from pre-processing up to electrophoresis by using a cartridge 200 proposed in this specification. The details of the cartridge 200 are described below.

The pre-processing integrated capillary electrophoresis device 100 includes a capillary array 400, a pump/buffer unit 450, a thermostatic unit 410, a heater 500, a liquid transfer pump 520, a control valve unit 550, an automatic sampler unit 600, a detection unit 700, a high-voltage power supply unit 800, and a controller 900. The details of such units are described below. It should be noted that the controller 900 controls the operation of each unit included in the pre-processing integrated capillary electrophoresis device 100. The cartridge 200 is mounted on a mount table (not shown), and the heater 500 is attached to the inside of the mount table.

[Configuration of Cartridge]

Figure 2:
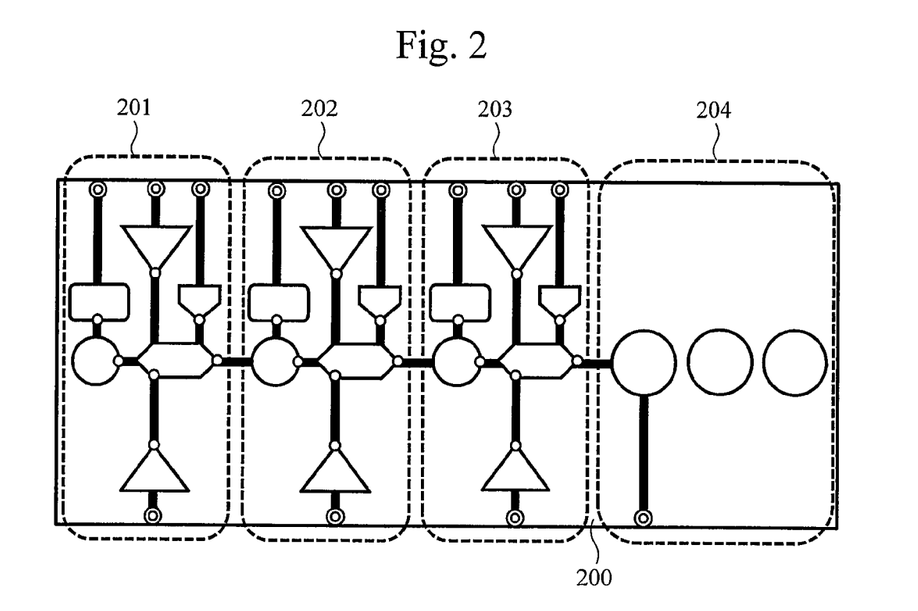
FIG. 2 shows an exemplary configuration of the top face of an integrated cartridge for a developing solution for pre-processing and electrophoresis in accordance with Embodiment 1.

The cartridge 200 used in this embodiment has a single flat substrate having flow channels and control valves formed on its surface. In this embodiment, a single cartridge 200 is used for a series of operations of from extraction of nucleic acids up to preparation of a phoresis sample. Each operation is fully automatically executed by the cooperative operation of each unit of the pre-processing integrated capillary electrophoresis device 100 as described in detail below. In this embodiment, a single cartridge 200 is used up in a single measurement in principle.

FIG. 2 shows the entire configuration of the cartridge 200 used in this embodiment. The cartridge 200 generally includes four blocks that are a nucleic acid extraction block 201 for use in a reaction of extracting nucleic acids from a biological sample, a PCR block 202 for use in amplifying and purifying the nucleic acids, a cycle sequence block 203 for use in labeling the nucleic acids through a cycle sequence reaction, and a phoresis block 204 for use in capillary electrophoresis. The configuration of each block and an operation method therefor are described below.

[Configuration of Capillary Array]

Figure 3:
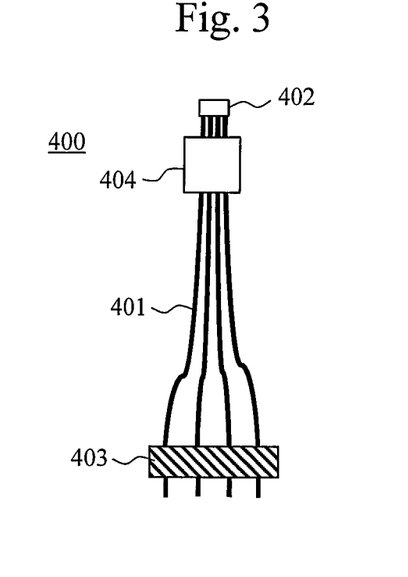
FIG. 3 shows the configuration of the top face of a capillary array.

FIG. 3 shows the configuration of the top face of the capillary array 400. The capillary array 400 has a bundle of one or more capillaries 401. Each capillary 401 has a glass tube with an inner diameter of several ten to several hundred micrometers and an outer diameter of several hundred micrometers, and the surface of the glass tube is coated with polyimide or the like. The inside of the capillary 401 is filled with a separation medium that provides a difference in electrophoretic velocity to a sample during electrophoresis.

A capillary head 402 is provided at one ends of the capillaries 401. The capillary head 402 is a member for bundling the capillaries 401. The pump/buffer unit 450 and the capillary array 400 are connected via the capillary head 402. A cathode electrode 403 is formed at the other ends of the capillaries 401. The cathode electrode 403 contacts a sample, a solution, or the like. It should be noted that a detection unit 404 is provided at a position close to the capillary head 402. The detection unit 404 reads a sample that has been electrophoretically separated in the capillaries 401. When the capillaries 401 are damaged or has degraded in quality, such capillaries 401 are replaced as needed.

[Configuration of Thermostatic Unit]

The thermostatic unit 410 has a function of maintaining the temperature of the capillary array 400 at a preset temperature during electrophoresis. The thermostatic unit 410 is a flat component with a configuration in which the capillaries 400 are sandwiched between a temperature control substrate with a heater attached thereto and a heat insulating material. The temperature control substrate also has a temperature feedback sensor attached thereto. Herein, one end of the capillary array 400 on the cathode electrode 403 side is fixed at the thermostatic unit 410. Accordingly, the tip end of the capillary head 402 can be fixed at a desired position.

[Configuration of Pump/Buffer Unit]

Figure 4:
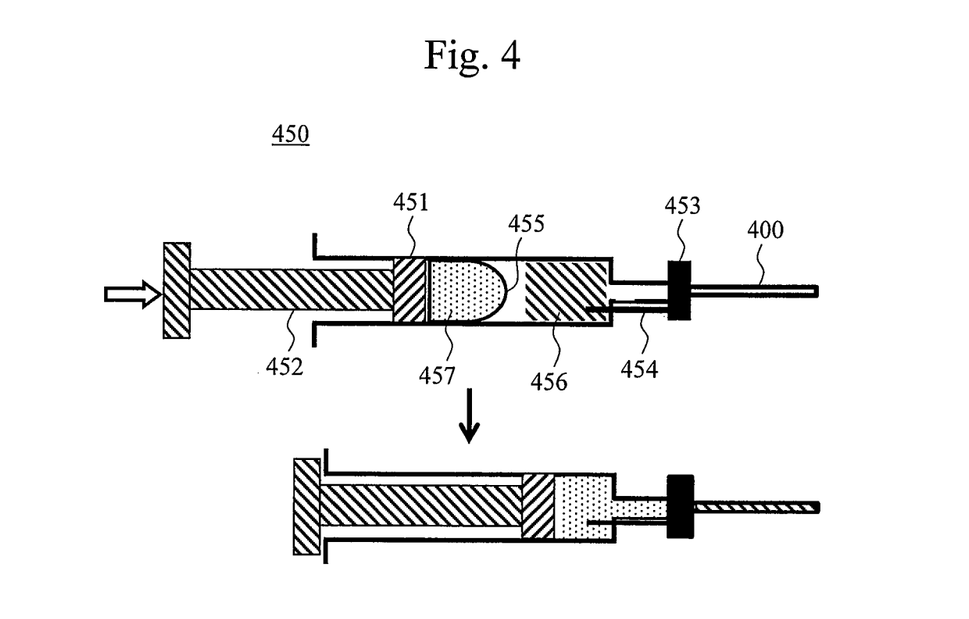
FIG. 4 shows an exemplary configuration of the cross-section of a pump/buffer unit.

The pump/buffer unit 450 is a pump used to fill the capillary array 400 (specifically, individual capillaries 401) with a separation medium such as a polymer.

FIG. 4 shows the detailed structure of the pump/buffer unit 450. The pump/buffer unit 450 has a disposer container 451, a piston 452 for hermetically sealing the container and applying pressure to the inside of the container, a valve 453 that connects a tip end of the disposer container 451 and the capillary array 400, and an anode electrode 454 fixed at the valve 453 or the piston 452.

A tip end of the anode electrode 454 protrudes inward from the bottom face (i.e., a plane having an output port) of the disposer container 451.

A separation medium 456 is stored in the disposer container 451 in a state in which the piston 452 is pulled (i.e., in the initial state). It should be noted that a small bag surrounded by a thin film 455 is attached to a tip end of the piston 452, and the inside of the bag is filed with an anode buffer solution 457. As described above, the inside of the disposer container 451 is divided into two blocks in the state in which the piston 452 is pulled. Thus, there is no possibility that the separation medium 456 will be mixed with the anode buffer solution 457.

In order to fill the capillary array 400 with the separation medium 456, the piston 452 is pushed into the inside of the disposer container 451 with pressure applied thereto from the outside. At this time, high pressure is applied to the inside of the disposer container 451. Accordingly, the capillaries 401 are filled with the separation medium 456 via the valve 453.

During electrophoresis, the piston 452 is further pressed into the inside of the disposer container 451 with pressure applied thereto. At this time, when the amount of stroke of the piston 452 exceeds a given amount, the tip end of the anode electrode 454 sticks out through the thin film 455. Accordingly, the separation medium 456 and the anode buffer solution 457 are mixed in the disposer container 451.

It should be noted that in the pump/buffer unit 450, the separation medium 456 and the anode buffer solution 457 may also be stored in different regions in a single component. However, the anode electrode 454 should be always in contact with the anode buffer solution 457.

[Configuration of Heater]

The heater 500 is used for heat' retention of a solution held in the cartridge 200 and temperature adjustment in heating cycles and the like. In the example shown in FIG. 1, the heater 500 is arranged inside or on the surface of the mount table of the cartridge 200. For example, the heater 500 and the cartridge 200 are fixed with a fastening device or the like.

[Configuration of Liquid Transfer Pump]

The liquid transfer pump 520 sends air or the like to the control valves formed in the cartridge 200, and applies pressure to or reduces pressure in the flow channels and the tanks in the cartridge, thereby adjusting transfer of a solution in the cartridge 200.

[Configuration of Control Valve Unit]

The control valve unit 550 is a mechanism unit that opens or closes the control valves formed in the cartridge 200.

[Configuration of Automatic Sampler Unit]

The automatic sampler unit 600 is a robot device for sequentially transporting the cartridge 200 to the initial set position, and then to the pre-processing reaction unit, and further to the sample introduction ends of the capillaries 400.

[Configuration of Detection Unit]

The detection unit 700 irradiates the detection unit 404 of the capillary array 400 with excitation light 701 output from a light source, such as a laser or a LED, and detects scattered light 702 and the like generated from the capillaries 401 by a detector 703. The detected light is output to a measuring device (not shown). The measuring device analyzes a sample on the basis of the signal intensity of the detected scattered light 702.

[Configuration of High-Voltage Power Supply Unit]

The high-voltage power supply unit 800 is connected to the anode electrode 454 and the cathode electrode 403, and executes electrophoresis by applying high voltage to the capillaries 401 filled with a polymer.

[Configuration of Controller]

The controller 900 controls the operation of each unit so that the heater 500, the liquid transfer pump 520, and the control valve unit 550 operate in cooperation with one another.

[Summary of Operations of from Pre-Processing to Electrophoresis]

Next, a series of operations that are automatically executed by the pre-processing integrated capillary electrophoresis device will be described.

(1) Pre-Processing Operation

Figure 5:
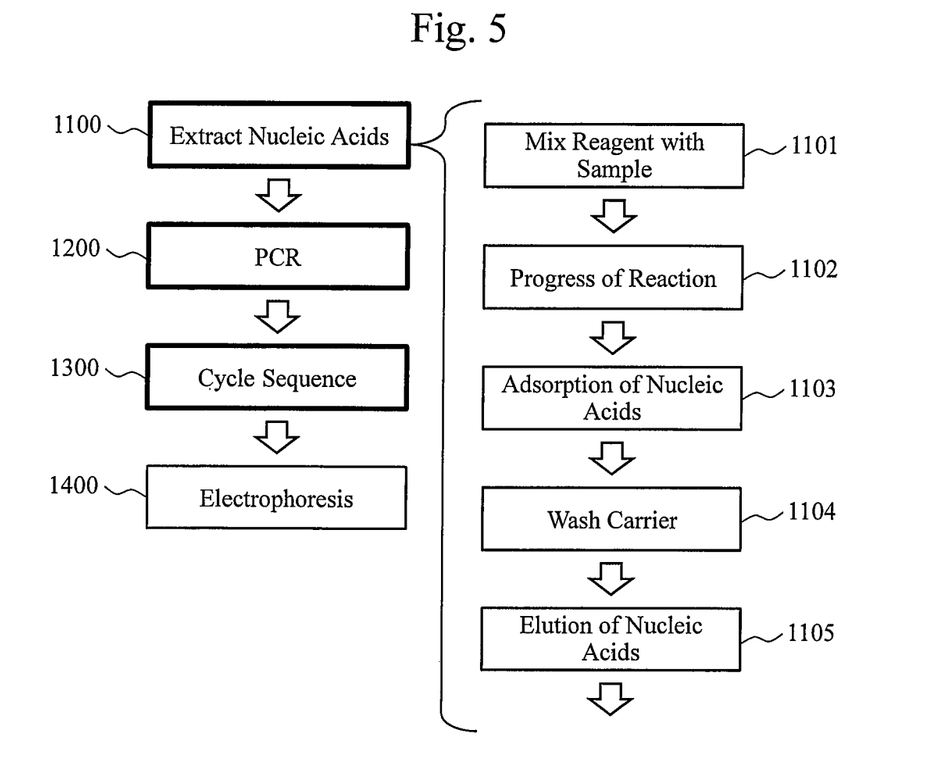
FIG. 5 illustrates the pre-processing steps in accordance with Embodiment 1.

Herein, a summary of pre-processing will be described with reference to FIG. 5. It should be noted that pre-processing is an operation of extracting nucleic acids from a biological sample, such as a swab or blood, and processing the sample for analysis (i.e., for conducting base sequence analysis through capillary electrophoresis). The pre-processing can be broadly divided into three steps that include extraction of nucleic acids 1100, a PCR reaction 1200, and a cycle sequence reaction 1300. It should be noted that depending on the target to be analyzed, capillary electrophoresis 1400 may be executed after only the extraction of nucleic acids 1100 and the PCR reaction 1200 are terminated as the pre-processing.

The three steps can be executed in accordance with the same procedures. That is, each step includes (1) mixing a reagent with a sample 1101, (2) progress of a reaction 1102, (3) adsorption of nucleic acids onto a carrier 1103, (4) washing of the carrier 1104, and (5) elution of nucleic acids 1105. Among them, (1) and (2) correspond to the execution of reactions, while (3) to (5) correspond to purification of reactants.

Hereinafter, control operations that are executed by the controller 900 in each stage will be described.

(1-1) Extraction of Nucleic Acids

In the extraction of nucleic acids 1100, the control operation 1101 of (1) is executed first. In the control operation 1101, a sample is first inserted into the cartridge 200. The sample is transferred to a reaction tank in which a reagent is stored and thus is mixed with the reagent. The sample is a biological sample, for example. Meanwhile, the reagent is a cell soluble solution, a buffer solution, or the like, for example.

Next, the control operation 1102 of (2) is executed. In the control operation 1102, the cartridge 200 is heated or cooled to an adequate reaction temperature by the heater 500. When the temperature is adjusted in this manner, the biological sample dissolves, and nucleic acids are thus exposed.

Then, the control operation 1103 of (3) is executed. In the control operation 1103, the dissolved sample is transferred to a carrier tank so that the sample is mixed with a carrier and the nucleic acids are adsorbed onto the surface of the carrier. Next, the control operation 1104 of (4) is executed. In the control operation 1104, a wash solution is transferred to the carrier tank so that the reagent and the sample other than the nucleic acids adsorbed on the carrier are washed away. It should be noted that the waste liquid is then transferred to a waste liquid tank. Finally, the control operation 1105 of (5) is executed. In the control operation 1105, an eluate is transferred to the carrier tank so that the nucleic acids adsorbed on the carrier are recovered.

(1-2) PCR Reaction

In the PCR reaction 1200, the control operation 1101 of (1) is also executed first. In the control operation 1101, the sample after the extraction of nucleic acids is transferred from the nucleic acid extraction block 201 to the PCR block 202. The sample is transferred to a reaction tank in which a reagent (i.e., primers, dNTP, buffer solution, or enzymes) is stored and thus is mixed with the reagent.

Next, the control operation 1102 of (2) is executed. In the control operation 1102, the temperature of the mixed solution in the cartridge 200 is heated or cooled to an adequate reaction temperature through heating cycles of the heater 500. Such temperature adjustment allows only the target region of nucleic acids to be amplified.

Then, the control operation 1103 of (3) is executed. In the control operation 1103, the reaction product is transferred to a carrier tank so that the reaction product is mixed with a carrier and the nucleic acids are adsorbed onto the surface of the carrier. Next, the control operation 1104 of (4) is executed. In the control operation 1104, a wash solution is transferred to the carrier tank so that the reagent and the sample other than the nucleic acids adsorbed on the carrier are washed away. It should be noted that the waste liquid is then transferred to a waste liquid tank. Finally, the control operation 1105 of (5) is executed. In the control operation 1105 herein, an eluate is transferred to the carrier tank so that the nucleic acids adsorbed on the carrier are recovered.

(1-3) Cycle Sequence Reaction

In the cycle sequence reaction 1300, the control operation 1101 of (1) is also executed first. In the control operation 1101 herein, a product of the PCR reaction is first transferred from the PCR block 202 to the cycle sequence block 203. The product from the PCR block 202 is transferred to a reaction tank in which a reagent (i.e., primers, fluorescently-labeled dNTP, enzymes, or buffer solution) is stored and thus is mixed with the reagent.

Next, the control operation 1102 of (2) is executed. In the control operation 1102, the temperature of the mixed solution in the cartridge 200 is heated or cooled to an adequate reaction temperature through heating cycles of the heater 500. Such temperature adjustment allows hybridization of fluorescently-labeled dNTP with the nucleic acids.

Then, the control operation 1103 of (3) is executed. In the control operation 1103, the reaction product is transferred to a carrier tank so that the reaction product is mixed with a carrier and the nucleic acids are adsorbed onto the surface of the carrier. Next, the control operation 1104 of (4) is executed. In the control operation 1104 herein, a wash solution is transferred to the carrier tank so that the reagent and the sample other than the nucleic acids adsorbed on the carrier are washed away. It should be noted that the waste liquid is then transferred to a waste liquid tank. Finally, the control operation 1105 of (5) is executed. In the control operation 1105, an eluate is transferred to the carrier tank so that that the nucleic acids adsorbed on the carrier are recovered. That is, excess fluorescence, primers, and the like are removed from the reaction product so that the nucleic acids are recovered. The nucleic acids are recovered into the phoresis block 204.

(2) Phoresis Operation

The nucleic acids recovered into the phoresis block 204 are subjected to the capillary electrophoresis 1400.

[Structure of Each Block and Liquid Transfer]

Next, the liquid transfer procedures in each block of the cartridge 200 will be specifically described. It should be noted that the general configurations and liquid transfer procedures of the nucleic acid extraction block 201, the PCR block 202, and the cycle sequence block 203 are the same. It should also be noted that the cartridge 200 is desirably made of a material on which a biological sample is difficult to be adsorbed, for example, quartz glass, PMMA, or polycarbonate.

Figure 6:
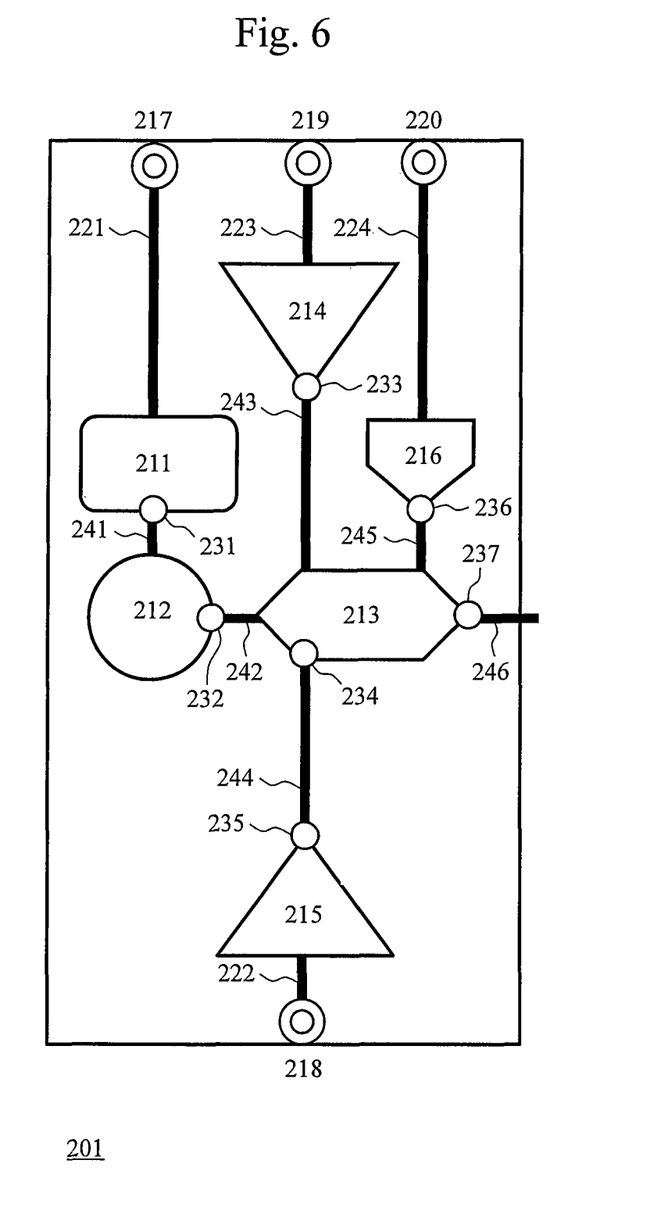
FIG. 6 shows an exemplary configuration of the top face of a nucleic acid extraction block.

FIG. 6 shows an exemplary configuration of the nucleic acid extraction block 201. The nucleic acid extraction block 201 includes a reagent tank 211 that stores a reagent, a reaction tank 212 that mixes an inserted biological sample with the reagent, a carrier tank 213 that stores a carrier for use in purifying a reaction product, a wash solution tank 214 that stores a wash solution for washing the carrier, a waste liquid tank 215 that recovers a solution other than nucleic acids from the carrier tank, and an eluate tank 216 that stores an eluate for recovering nucleic acids from the carrier.

For the reagent tank 211, a hermetically sealed structure is adopted so that the cartridge can be transported with a reagent stored in the reagent tank 211. Meanwhile, it is also possible to conduct analysis by injecting any given reagent into an empty reagent tank 211 immediately before starting analysis.

Flow channels 241 to 246 and control valves 231 to 237 for controlling opening and closing of the flow channels are provided between the tanks 211 to 216. It should be noted that the flow channel 246 is a flow channel that connects the nucleic acid extraction block 201 and the PCR block 202. Besides, the nucleic acid extraction block 201 has formed therein ports 217 to 220 for use in transferring a solution with pressure applied by the liquid transfer pump 520, and port flow channels 221 to 224. The port flow channels 221 to 224 are flow channels for individually connecting the ports 217 to 220 and their respective corresponding tanks.

The control valve 231 is arranged in a flow channel 241 that connects the reagent tank 211 and the reaction tank 212. The control valve 232 is arranged in a flow channel 242 that connects the reaction tank 212 and the carrier tank 213. The control valve 233 is arranged in a flow channel 243 that connects the wash solution tank 214 and the carrier tank 213. The control valve 234 and the control valve 235 are arranged in a flow channel 244 that connects the carrier tank 213 and the waste liquid tank 215. The control valve 236 is arranged in a flow channel 245 that connects the eluate tank 216 and the carrier tank 213. The control valve 237 is arranged in a flow channel 246 that connects the carrier tank 213 and the PCR block 202.

The carrier tank 213 is connected to the reaction tank 212, the wash solution tank 214, the waste liquid tank 215, and the eluate tank 216 via the different flow channels 242, 243, 244, and 245, respectively. It should be noted that the flow directions of all flow channels are determined in advance, and back flow is not allowed in principle.

The reagent tank 211, the wash solution tank 214, the waste liquid tank 215, and the eluate tank 216 are connected to the ports 217, 219, 218, and 220 via the port flow channels 221, 223, 222, and 224, respectively.

A carrier arranged in the carrier tank 213 is desirably the one on which nucleic acids are particularly easily adsorbed, such as glass beads, glass wool, or porous glass. In order to further increase the degree of purification, a method can be used that uses primers, which have biotin added thereto in advance, for reaction and modifies the surface of the carrier tank 213 with streptavidin. The wash solution contains a high concentration of organic solvent, such as alcohol, and removes components other than nucleic acids from the carrier by washing the carrier a plurality of times.

Figure 7:
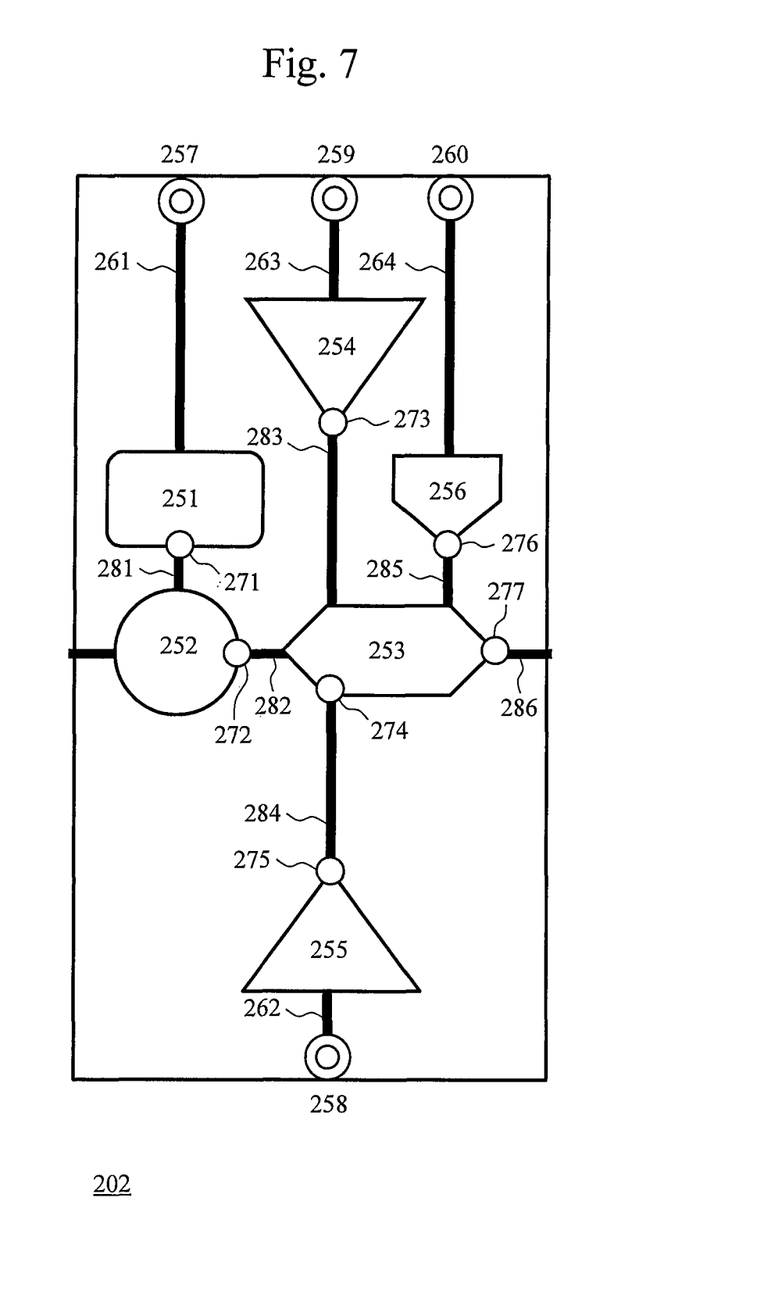
FIG. 7 shows an exemplary configuration of the top face of a PCR block.

FIG. 7 shows an exemplary configuration of the PCR block 202. The PCR block 202 includes a reagent tank 251 that stores a reagent, a reaction tank 252 that mixes a product of the nucleic acid extraction block 201 with the reagent and executes heating cycles, a carrier tank 253 that stores a carrier for use in purifying a reaction product, a wash solution tank 254 that stores a wash solution for washing the carrier, a waste liquid tank 255 that recovers a solution other than nucleic acids from the carrier tank, and an eluate tank 256 that stores an eluate for recovering nucleic acids from the carrier.

Flow channels 281 to 286 and control valves 271 to 277 for controlling opening and closing of the flow channels are provided between the tanks 251 to 256. It should be noted that the flow channel 286 is a flow channel for connecting the PCR block 202 and the cycle sequence block 203. Besides, the PCR block 202 also has formed therein ports 257 to 260 for use in transferring a solution with pressure applied by the liquid transfer pump 520, and port flow channels 261 to 264. The port flow channels 261 to 264 are flow channels for individually connecting the ports 257 to 260 and their respective corresponding tanks. In the PCR block 202, the flow directions of all flow channels are also determined in advance, and back flow is not allowed in principle.

Figure 8:
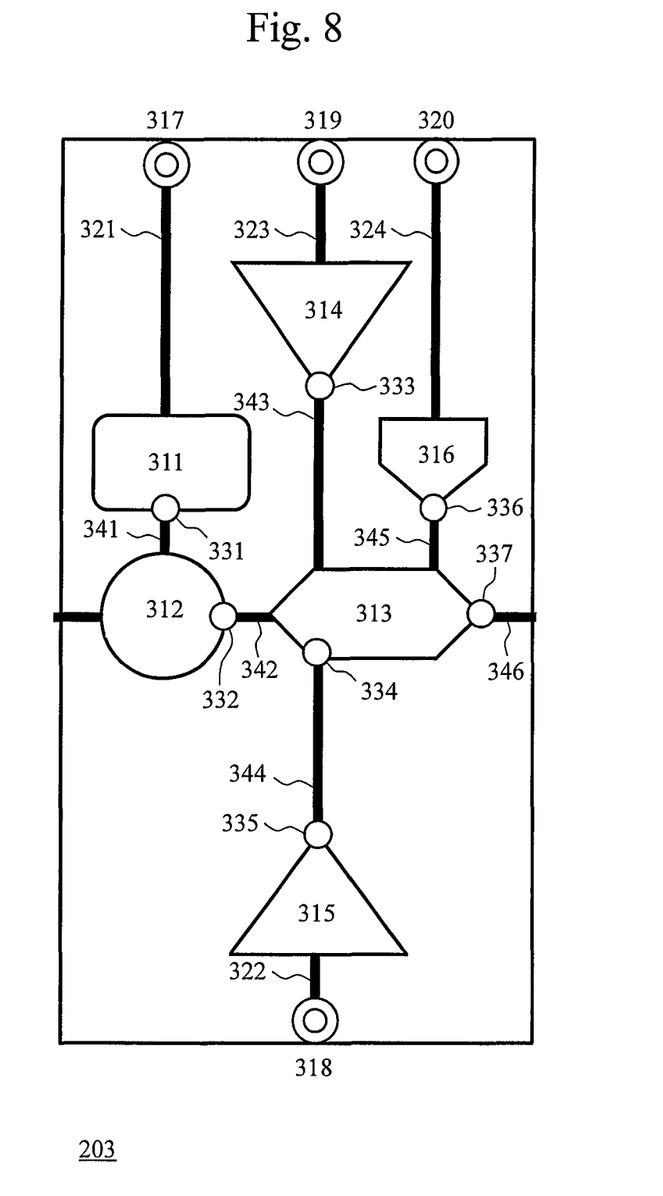
FIG. 8 shows an exemplary configuration of the top face of a cycle sequence block.

FIG. 8 shows an exemplary configuration of the cycle sequence block 203. The cycle sequence block 203 includes a reagent tank 311 that stores a reagent, a reaction tank 312 that mixes a product of the PCR block 202 with the reagent and executes heating cycles, a carrier tank 313 that stores a carrier for use in purifying a reaction product, a wash solution tank 314 that stores a wash solution for washing the carrier, a waste liquid tank 315 that recovers a solution other than nucleic acids from the carrier tank, and an eluate tank 316 that stores an eluate for recovering nucleic acids from the carrier.

Flow channels 341 to 346 and control valves 331 to 337 for controlling opening and closing of the flow channels are provided between the tanks 311 to 316. It should be noted that the flow channel 346 is a flow channel for connecting the cycle sequence block 203 and the phoresis block 204. Besides, the cycle sequence block 203 also has formed therein ports 317 to 320 for use in transferring a solution with pressure applied by the liquid transfer pump 520, and port flow channels 321 to 324. The port flow channels 321 to 324 are flow channels for individually connecting the ports 317 to 320 to their respective corresponding tanks. In the cycle sequence block 203, the flow directions of all flow channels are also determined in advance, and back flow is not allowed in principle.

Figure 9:
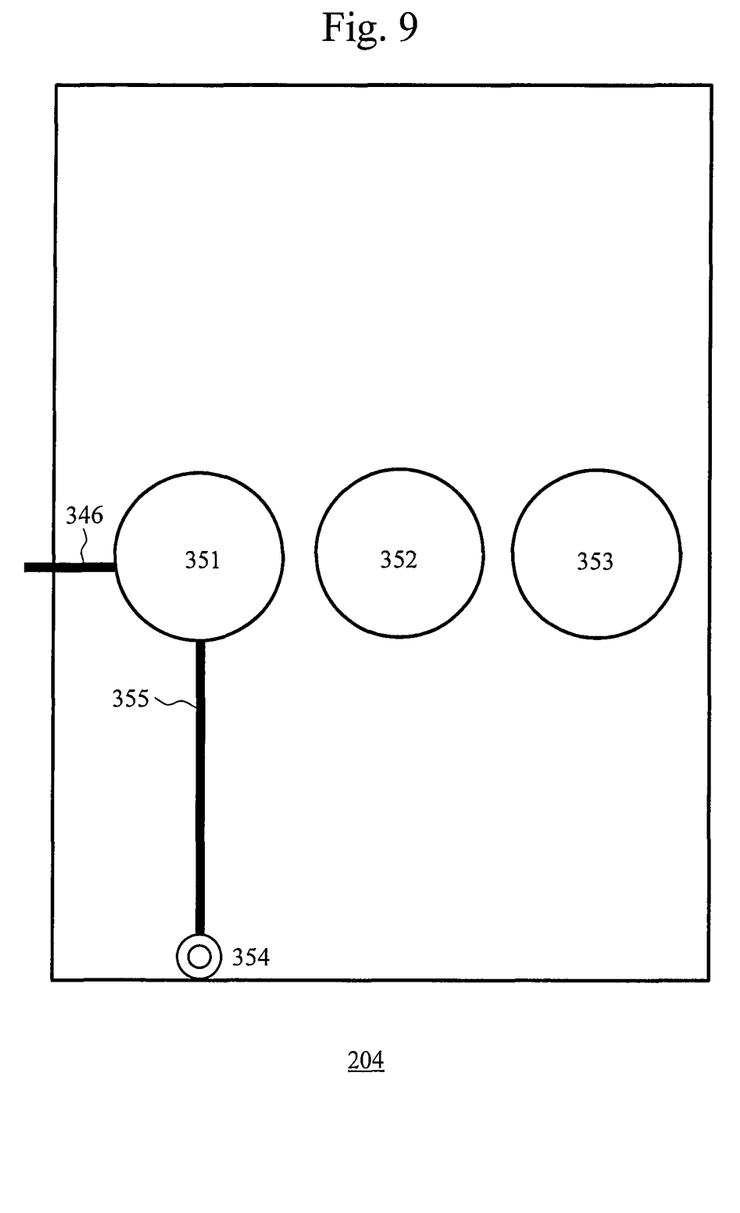
FIG. 9 shows an exemplary configuration of the top face of a phoresis block.

FIG. 9 shows an exemplary configuration of the phoresis block 204. The phoresis block 204 includes a phoretic solution tank 351, a cathode buffer solution tank 352 that stores a buffer solution containing an electrolyte, and a wash solution tank 353 that stores a wash solution for washing the capillaries. Among them, the phoretic solution tank 351 is connected to the cycle sequence block 203 via the flow channel 346. Besides, the phoresis block 204 also has formed therein a port 354 for use in transferring a solution with pressure applied by the liquid transfer pump 520, and a port flow channel 355. The port flow channel 355 connects the port 354 and the phoresis tank 351.

This embodiment has described a case where a wash solution tank and a waste liquid tank in each of the nucleic acid extraction block 201 to the cycle sequence block 203 are individually formed, as shown in FIGS. 6 to 8. However, the wash solution tank and the waste liquid tank in each block may also be combined as a single tank. In addition, although this embodiment has described a case where the number of blocks that constitute the cartridge 200 is four, the number of blocks may be increased or reduced depending on the sample to be analyzed or depending on with which type of sample analysis is started.

[Opening/Closing of Control Valves Along with Liquid Transfer]

Hereinafter, the procedures for executing pre-processing and capillary electrophoresis using the cartridge 200 will be described. A series of procedures of from pre-processing up to capillary electrophoresis is basically implemented by a combination of mixture of a reagent, which is effected by transfer of a liquid, and heat treatment. The following description is based on the assumption that a pump pressing method, which is the most common method, is used for transferring a liquid.

Initially, the control valves and the ports mounted on the cartridge 200 are all in the closed position, and operations of opening them are performed as needed. A control valve in the closed position has a mechanism of not passing solutions and the like therethrough but passing gas such as air therethrough. As a control valve with this type of property is already known, detailed description thereof is omitted herein.

Transfer of a solution in each of the nucleic acid extraction block 201, the PCR block 202, and the cycle sequence block 203 is completed by sequentially performing five times of liquid transfer operations in each block. Herein, an example of the first nucleic acid extraction block 201 will be described. The following description is also true of the liquid transfer operations in the PCR block 202 and the cycle sequence block 203.

Operation (1)

First, a biological sample, such as a swab or blood, is inserted into the reaction tank 212, and the tank is covered with a seal or the like so as to be hermetically sealed. In such a state, the control valve 231 and the ports 217 and 218 are opened so that air is injected through the port 217. Then, air sequentially flows through the port 217→the reagent tank 211→the reaction tank 212→the carrier tank 213→the waste liquid tank 215→the port 218. When air is injected into the port 217, a reagent stored in the reagent tank 211 flows into the reaction tank 212 through the flow channel 241, and is then mixed with the biological sample. At this time, the cartridge 200 may be heated with the heater 500 as needed so that the temperature of the mixed solution in the reaction tank 212 is adjusted to an adequate temperature.

Operation (2)

Next, air is further injected through the port 217 with the control valve 232 in the open position. It should be noted that the flow channel of air is the same as that in the operation (1). In such a case, the mixed solution of the biological sample and the reagent in the reaction tank 212 flows into the carrier tank 213 via the flow channel 242. At this time, nucleic acids in the mixed solution stick to the carrier in the carrier tank 213.

Operation (3)

Next, the control valve 232 and the port 217 are closed, and the control valves 233 to 235 and the port 219 are opened. It should be noted that the port 218 remains open. Air is injected through the port 219 in such a state. Then, air sequentially flows through the port 219→the wash solution tank 214→the carrier tank 213→the waste liquid tank 215→the port 218. When air is injected into the port 219, the mixed solution in the carrier tank 213 flows out to the waste liquid tank 215 via the flow channel 244. Instead, a wash solution stored in the wash solution tank 214 flows into the carrier tank 213 via the flow channel 243. When injection of air into the port 219 is further continued, the wash solution stored in the carrier tank 213 is entirely transferred to the waste liquid tank 215. After that, the control valves 233 to 235 are closed to avoid back flow and mixture. Repeating such operations a plurality of times can increase the effect of purification.

Operation (4)

Next, the port 219 is closed and the control valve 236 and the port 220 are opened. Herein, the port 218 remains open. Then, air sequentially flows through the port 219→the wash solution tank 214→the carrier tank 213→the waste liquid tank 215→the port 218. When air is injected through the port 220, an eluate stored in the eluate tank 216 flows into the carrier tank 213 via the flow channel 245.

Operation (5)

After the eluate in the eluate tank 216 has flowed into the carrier tank 213, the tank is left for a time enough for the nucleic acids, which have once stuck to the carrier, to dissolve in the eluate. After that, the port 218 is closed, and the control valve 237 and the port 258 are opened. At this time, the port 258 provided in the PCR block 202 is opened. Then, air sequentially flows through the port 220→the eluate tank 216→the carrier tank 213→the reaction tank 252→the carrier tank 253→the waste liquid tank 255→the port 258. In such a state, air is injected through the port 220. Then, the solution in the carrier tank 213 flows into the reaction tank 252 in the next block, that is, the PCR block 202 via the flow channel 246. When liquid transfer from the nucleic acid extraction block 201 to the PCR block 202 is completed as described above, the ports 220 and 258 are closed.

In this embodiment, the PCR block 202 and the cycle sequence block 203 each have the same structure as the nucleic acid extraction block 201. Thus, similar operations to the operations (1) to (5) described above are repeatedly performed in each of the PCR block 202 and the cycle sequence block 203.

Next, transfer of a solution in the phoresis block 204 will be described. A denaturant, such as formamide, is encapsulated in the phoretic solution tank 351 in the phoresis block 204. The eluate transferred from the cycle sequence block 203 is mixed with the denaturant in the phoretic solution tank 351. It should be noted that in the phoresis block 204, the cathode buffer solution tank 352 and the wash solution tank 353 are provided in addition to the phoretic solution tank 351. An opening of each tank is covered with a thin film, such as a seal, to avoid evaporation of the solution from each tank and contamination from the outside.

When capillary electrophoresis is conducted, the tip ends of the capillaries 401 are caused to penetrate through the thin film that covers the opening of the phoretic solution tank 351 so that the tip ends of the capillaries 401 are immersed in a solution in the tank. Alternatively, the thin film may be ruptured not by the tip ends of the capillaries but by a needle that is separately prepared. As a further alternative, the opening of each tank may be covered with not a seal but a rubber film with a slit so that the tip ends of the capillaries may be inserted through the slit.

[Processing Operation of Pre-Processing Integrated Capillary Electrophoresis Device]

Figure 10:
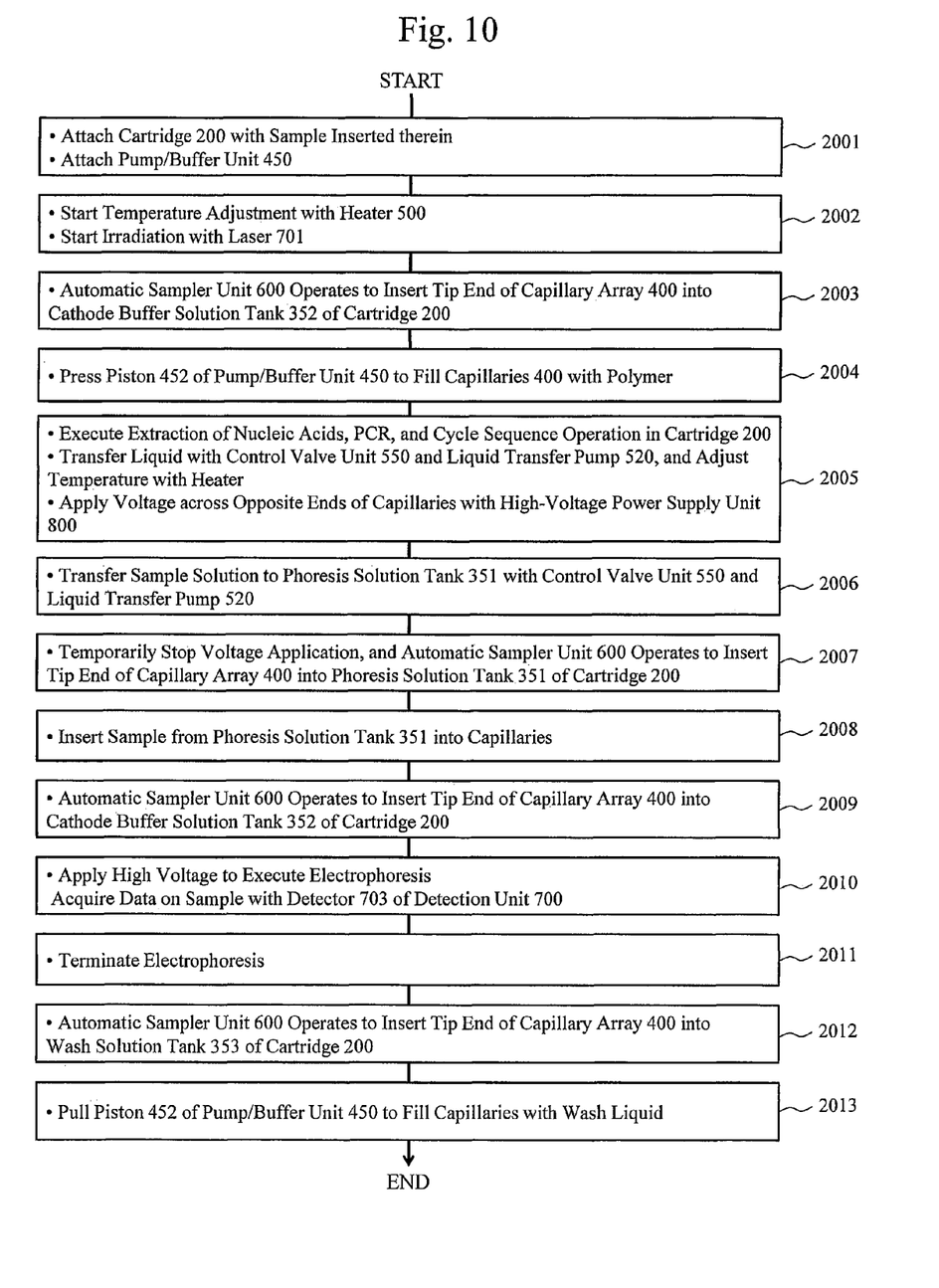
FIG. 10 is a flowchart illustrating the operation procedures of a pre-processing integrated capillary electrophoresis device.

FIG. 10 shows the operation procedures of the pre-processing integrated capillary electrophoresis device 100 in accordance with this embodiment. Each step will be described with supplementary explanations of the drawings.

(Step 2001)

As a premise, the cartridge 200 with a sample introduced therein is attached to the mount table of the pre-processing integrated capillary electrophoresis device 100. In addition, the pump/buffer unit 450 is attached to the pre-processing integrated capillary electrophoresis device 100. When power of the body of the device is turned on in such a state, the present operation procedures are started. First, the cartridge 200 in which a biological sample and a reagent are encapsulated is fixed on the automatic sampler unit 600. At this time, the bottom face of the cartridge 200 is in contact with the heater 500. The control valves 231 to 237, 271 to 277, and 331 to 337 of the cartridge 200 are connected to the control valve unit 550, while the ports 217 to 220, 257 to 260, and 317 to 320 are connected to the liquid transfer pump 520. In addition, the pump/buffer unit 450 is connected to one end of the capillary array 400 and to the high-voltage power supply unit 800.

(Step 2002)

In such a state, temperature adjustment by the heater 500 is started. The temperature may be manually set by a user each time the device is used, or be automatically set to a predetermined temperature in accordance with the measurement to be conducted. In this stage, irradiation with laser 701 is also started. It should be noted that an output immediately after laser irradiation is started is unstable. Thus, in order to maintain the detection sensitivity, laser irradiation may be started in advance before electrophoresis is started.

(Step 2003)

An arm of the automatic sampler unit 600, which fixes the three units: the cartridge 200, the heater 500, and the control valve unit 520, moves to immerse the tip end of the capillary array 400 in the cathode buffer solution tank 352.

(Step 2004)

Next, external force is applied to the piston 452 of the pump/buffer unit 450 manually or by automatic control, so that the capillary array 400 is filled with the separation medium 456 stored in the pump/buffer unit 450. At the same time, the anode electrode 454 becomes immersed in the anode buffer solution 457.

(Step 2005)

In the cartridge 200, extraction of nucleic acids, a PCR reaction, and a cycle sequence reaction are continuously performed. The execution methods therefor are as described above. In addition, voltage is applied across opposite ends of the capillaries by the high-voltage power supply unit 800. Such operation is called pre-run. When pre-run is performed for a long time, the analysis performance of capillary electrophoresis can be advantageously improved.

(Step 2006)

A sample in the cycle sequence block 203 is transferred to the phoretic solution tank 351 located at the next stage by the control valve unit 550 and the liquid transfer pump 520. When a reagent, a mixed solution, and a reaction solution are transferred in the cartridge 200, it is possible to adjust the amount of liquid transferred by adjusting the amount of air injected from the pump 520. It is desirable that an eluate in each block be not entirely transferred to the next tank but be partially stored. By doing so, it becomes possible to execute analysis later again from the middle stage of the process.

(Step 2007)

Herein, application of voltage is temporarily stopped. In such a state, the automatic sampler unit 600 operates to insert the tip end of the capillary array 400 into the phoretic solution tank 351.

(Step 2008)

Low voltage is applied across the opposite ends of the capillary array from the high-voltage power supply unit 800 for a short time, whereby an adequate amount of sample can be introduced into the capillary array 400 filled with the separation medium.

(Step 2009) The automatic sampler unit 600 operates again to immerse the tip end of the capillary array 400 in a cathode buffer solution encapsulated in the cathode buffer solution tank 352.

(Step 2010)

High voltage is applied to the capillary array 400 from the high-voltage power supply unit 800 to execute electrophoresis. During the electrophoresis, the detection unit 404 of the capillaries 401 is irradiated with excitation light 701. The detector 703 detects a sample emitting fluorescence in response to the excitation light 701, and outputs detection results to a measuring device (not shown). The measuring device analyzes the sample on the basis of the detection results.

(Step 2011)

At this stage, the electrophoresis terminates.

(Step 2012)

After termination of the application of voltage, the automatic sampler unit 600 operates to immerse the tip end of the capillary array 400 in the wash solution tank 353. Wash water for washing the tip ends and the inside of the capillaries is encapsulated in the wash solution tank 353.

(Step 2013)

The piston 452 of the pump/buffer unit 450 is pulled manually or by automatic control so that the inside of the capillary array is filled with the wash solution. When such operation is repeated a number of times, the washing effect can be improved.

CONCLUSION

As described above, when the cartridge 200 in accordance with this embodiment is used in combination with the pre-processing (e.g., extraction of nucleic acids, an amplification reaction, and a cycle sequence reaction) integrated capillary electrophoresis device 100, it becomes possible to execute automation of all reaction steps of from pre-processing up to electrophoresis using a single device and a single cartridge.

Embodiment 2

This embodiment shows an exemplary configuration of the cartridge 200 that is suitable for a case where capillary electrophoresis is executed on purified nucleic acids to analyze fragments. The basic configuration and operation of the pre-processing integrated capillary electrophoresis device 100 are similar to those in Embodiment 1. Hereinafter, the difference between this embodiment and Embodiment 1 will be mainly described.

Figure 11:
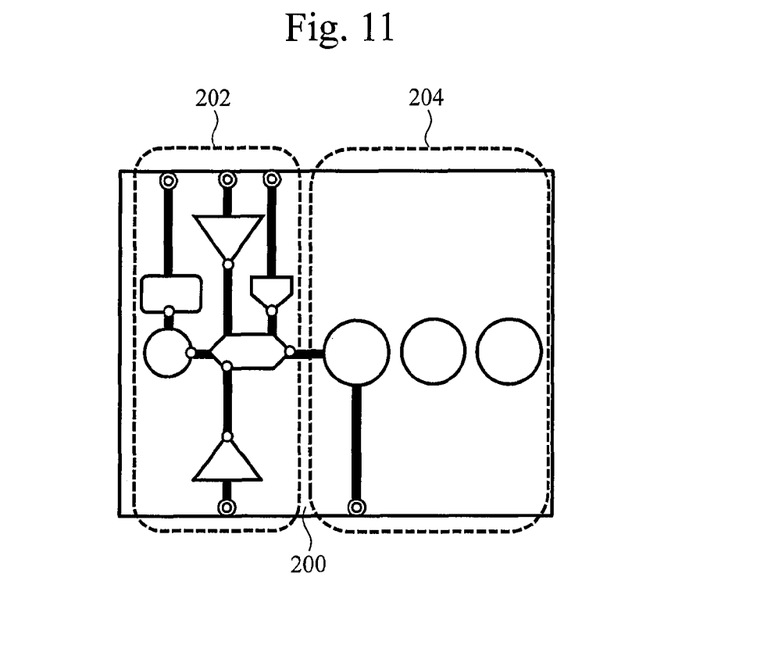
FIG. 11 shows an exemplary configuration of the top face of a cartridge in accordance with Embodiment 2.

FIG. 11 shows an exemplary configuration of the cartridge 200 in accordance with this embodiment. The cartridge 200 shown in FIG. 11 includes only the PCR block 202 and the phoresis block 204. The nucleic acid extraction block 201 and the cycle sequence block 203 are omitted herein.

In this embodiment, a solution of purified nucleic acids is introduced into the reaction tank 252, and thereafter, the tank is covered with a seal or the like to be hermetically sealed, so that a processing step is started. The subsequent steps are the same as those in Embodiment 1. In this case also, similar advantageous effects to those in Embodiment 1 can be provided.

Embodiment 3

In this embodiment, a different reagent is encapsulated in the tank to enable execution of another analysis. As described previously, the reagent tank 251 in the PCR block 202 is hermetically sealed so that the cartridge can be transported with a reagent stored in the reagent tank 251. Meanwhile, it is also possible to conduct analysis by injecting any given reagent into an empty reagent tank 251 immediately before starting analysis.

As an example, a method for performing STR (short tandem repeat) analysis on purified nucleic acids will be described. It should be noted that the basic configuration and operation of the pre-processing integrated capillary electrophoresis device 100 are similar to those in Embodiment 2.

This embodiment differs from Embodiment 2 in that a mixed solution of enzymes, dNTP, a buffer solution, and the like for use in a PCR reaction are encapsulated in the reagent tank 251, while a fluorescently-labeled primer mixed solution corresponding to a STR region is encapsulated in the reaction tank 252. In such a case also, similar advantageous effects to those in Embodiment 2 can be provided.

Embodiment 4

This embodiment will describe a configuration in which a PCR reaction and a cycle sequence reaction can be performed on purified nucleic acids. The basic configuration and operation of the pre-processing integrated capillary electrophoresis device 100 are similar to those in Embodiment 1. Hereinafter, the difference between Embodiment 1 and this embodiment will be mainly described.

Figure 12:
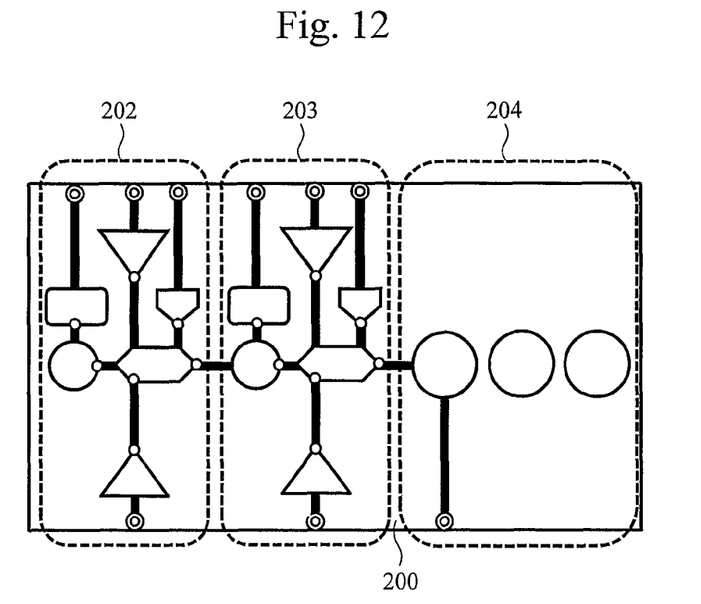
FIG. 12 shows an exemplary configuration of the top face of a cartridge in accordance with Embodiment 4.

FIG. 12 shows an exemplary configuration of the cartridge 200 in accordance with this embodiment. The cartridge 200 shown in FIG. 12 includes only three: the PCR block 202, the cycle sequence block 203, and the phoresis block 204. The nucleic acid extraction block 201 is omitted herein.

In this embodiment, a reaction operation is started in a state in which a solution of purified nucleic acids is inserted in the reaction tank 252 and the reaction tank 252 is covered with a seal or the like and thus is hermetically sealed. The subsequent steps are similar to those in Embodiment 1. In such a case also, similar advantageous effects to those in Embodiment 1 can be provided.

Other Embodiments

It should be noted that the present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add/remove/substitute a configuration of another embodiment.

REFERENCE SIGNS LIST

100 Pre-processing integrated capillary electrophoresis device
200 Cartridge
201 Nucleic acid extraction block
202 PCR block
203 Cycle sequence block
204 Phoresis block
211, 251, 311 Reagent tank
212, 252, 312 Reaction tank
213, 253, 313 Carrier tank
214, 254, 314 Wash solution tank
215, 255, 315 Waste liquid tank
216, 256, 316 Eluate tank
217 to 220, 257 to 260, 317 to 320, and 354 Port
221 to 224, 261 to 264, and 321 to 324 Port flow channel
231 to 237, 271 to 277, 331 to 337 Control valve
241 to 246, 281 to 286, 341 to 346, and 351 Phoretic solution tank
352 Cathode buffer solution tank
353 Wash solution tank
355 Flow channel
400 Capillary array
401 Capillary
402 Capillary head
403 Cathode electrode
404 Detection unit
410 Thermostatic unit
450 Pump/buffer unit
451 Disposer container
452 Piston
453 Valve
454 Anode electrode
455 Thin film
456 Separation medium (polymer)
457 Anode buffer solution
500 Heater
520 Liquid transfer pump
550 Control valve unit
600 Automatic sampler unit
700 Detection unit
701 Excitation light
702 Scattered light
703 Detector
800 High-voltage power supply unit
900 Controller

The invention claimed is:

1. A pre-processing integrated capillary electrophoresis device comprising:
a mount table;
a pre-processing/electrophoresis integrated cartridge which mounts on the mount table, the cartridge including a plurality of block structures corresponding to a step of extracting a nucleic acid from a biological sample, a step of performing a PCR reaction on a target region of the nucleic acid, and a step of performing a cycle sequence reaction on the nucleic acid that is amplified, the block structures including:
(1) a first block having a reaction tank into which the biological sample is injected, a reagent tank that stores a reagent for use in a reaction with the biological sample, a plurality of flow channels that connect the tanks, a plurality of control valves arranged in the flow channels, and a flow channel that connects a preceding reaction tank in a preceding one of the block structures located at a preceding stage of the first block and a next reaction tank in a next one of the block structures located at a next stage, and (2) a second block having a phoretic solution tank that stores a phoretic solution, a cathode buffer solution tank that stores a buffer solution containing an electrolyte for use in capillary electrophoresis, a wash solution tank that stores a wash solution for washing a tip end of a capillary to avoid contamination between samples, a flow channel that connects a preceding carrier tank in a preceding one of the block structures located at a preceding stage of the second block and the phoretic solution tank, and a control valve for the flow channel;

a temperature adjustment mechanism for adjusting a temperature of a solution in the cartridge;

a capillary electrophoresis mechanism; and a controller configured to control opening and closing of the control valves to control liquid transfer in and between the first and second blocks, and control an electrophoresis operation by controlling the capillary electrophoresis mechanism, wherein at least one of the step of extracting a nucleic acid from the biological sample, the step of performing a PCR reaction on a target region of the nucleic acid, or the step of performing a cycle sequence reaction on the nucleic acid that is amplified, and a capillary electrophoresis step of analyzing the nucleic acid are all executed automatically.

2. The pre-processing integrated capillary electrophoresis device according to claim 1, wherein when the first block has a block structure corresponding to the step of performing the PCR reaction and the second block has a block structure corresponding to the electrophoresis step, and the controller is configured to start pre-processing after injecting a solution of a nucleic acid purified from the biological sample into the reaction tank in the first block.

3. The pre-processing integrated capillary electrophoresis device according to claim 1, wherein when the first block has two block structures corresponding to the step of performing the PCR reaction and the step of performing a cycle sequence reaction, respectively, and the second block has a block structure corresponding to the electrophoresis step, the controller is configured to start pre-processing after injecting a solution of a nucleic acid purified from the biological sample into the reaction tank in the first block.

4. The pre-processing integrated capillary electrophoresis device according to claim 1, further comprising:

a pump/buffer unit including:

(1) a dispenser container that holds a buffer solution and a polymer to be supplied to the capillary in the capillary electrophoresis mechanism, an output port of the dispenser container being connected to the tip end of the capillary, (2) a partition that prevents mixture of the buffer solution and the polymer in the dispenser container in an initial state, (3) a piston to apply pressure to and reduce pressure in the dispenser container, and (4) an anode terminal having a tip end arranged in a manner protruding inward the dispenser container, the tip end of the anode terminal being arranged to stick out through the partition upon application of pressure by the piston, thereby mixing the buffer solution and the polymer.

5. A pre-processing/electrophoresis integrated cartridge comprising:

a plurality of block structures corresponding to a step of extracting a nucleic acid from a biological sample, a step of performing a PCR reaction on a target region of the nucleic acid, and a step of performing a cycle sequence reaction on the nucleic acid that is amplified, the block structures including:

(1) a first block having a reaction tank into which the biological sample is injected, a reagent tank that stores a reagent for use in a reaction with the biological sample, a plurality of flow channels that connect the tanks, a plurality of control valves arranged in the flow channels, and a flow channel that connects a preceding reaction tank in a preceding one of the block structures located at a preceding stage and a next reaction tank in a next one of the block structures located at a next stage, and (2) a second block having a phoretic solution tank that stores a phoretic solution, a cathode buffer solution tank that stores a buffer solution containing an electrolyte for use in capillary electrophoresis, and a wash solution tank that stores a wash solution for washing a tip end of a capillary to avoid contamination between samples, a flow channel that connects a preceding carrier tank in preceding one of the block structures located at a preceding stage and the phoretic solution tank, and a control valve for the flow channel.

6. The pre-processing/electrophoresis integrated cartridge according to claim 5, wherein the first block has a block structure corresponding to the step of performing the PCR reaction and the second block has a block structure corresponding to the electrophoresis step.

7. The pre-processing/electrophoresis integrated cartridge according to claim 5, wherein the first block has two block structures corresponding to the step of performing the PCR reaction and the step of performing a cycle sequence reaction, respectively, and the second block has a block structure corresponding to the electrophoresis step.

8. A pre-processing integrated capillary electrophoresis method, the method comprising:

providing a pre-processing/electrophoresis integrated cartridge, the cartridge including a plurality of block structures corresponding to a step of extracting a nucleic acid from a biological sample, a step of performing a PCR reaction on a target region of the nucleic acid, and a step of performing a cycle sequence reaction on the nucleic acid that is amplified, the block structures including:

(1) a first block having a reaction tank into which the biological sample is infected, a reagent tank that stores a reagent for use in a reaction with the biological sample, a plurality of flow channels that connect the tanks, a plurality of control valves arranged in the flow channels, and a flow channel that connects a preceding reaction tank in a preceding one of the block structures located at a preceding stage and a next reaction tank in a next one of the block structures located at a next stage, and (2) a second block having a phoretic solution tank that stores a phoretic solution, a cathode buffer solution tank that stores a buffer solution containing an electrolyte for use in capillary electrophoresis, a wash solution tank that stores a wash solution for washing a tip end of a capillary to avoid contamination between samples, a flow channel that connects a preceding carrier tank in a preceding one of the block structures located at a preceding stage and the phoretic solution tank, and a control valve for the flow channel;

providing a temperature adjustment mechanism for adjusting a temperature of a solution in the cartridge, and a capillary electrophoresis mechanism;

controlling opening and closing of control valves to control liquid transfer in and between the first and second blocks;

automatically controlling execution of at least one of the step of extracting the nucleic acid from the biological sample, the step of performing the PCR reaction on the target region of the nucleic acid, or the step of performing the cycle sequence reaction on the nucleic acid that is amplified; and automatically controlling execution of an electrophoresis operation by controlling the capillary electrophoresis mechanism.

9. The pre-processing integrated capillary electrophoresis method according to claim 8, wherein the automatic control starts after injecting a solution of the nucleic acid purified from the biological sample into a reaction tank in the block structures.

10. The pre-processing integrated capillary electrophoresis method according to claim 8, wherein when the first block corresponds to the step of performing a PCR reaction and the step of performing a cycle sequence reaction, and the automatic control starts after injecting a solution of the nucleic acid purified from the biological sample into a reaction tank in the block structures.

* * * * *